United States Patent
Nakanishi et al.

(10) Patent No.: US 8,731,269 B2
(45) Date of Patent: May 20, 2014

(54) METHOD AND SYSTEM FOR SUBSTANTIALLY REDUCING ARTIFACTS IN CIRCULAR CONE BEAM COMPUTER TOMOGRAPHY (CT)

(75) Inventors: Satoru Nakanishi, Tochigi-ken (JP); Be-Shan Chiang, Buffalo Grove, IL (US); Alexander Zamyatin, Hawthorn Woods, IL (US)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 59 days.

(21) Appl. No.: 13/276,841

(22) Filed: Oct. 19, 2011

(65) Prior Publication Data

US 2013/0101192 A1    Apr. 25, 2013

(51) Int. Cl.
G06K 9/00    (2006.01)
A61B 6/00    (2006.01)
A61B 5/00    (2006.01)

(52) U.S. Cl.
USPC .................. 382/131; 378/4; 378/21; 600/425

(58) Field of Classification Search
USPC ......... 382/128, 129, 130, 131, 132, 133, 134; 378/4, 8, 21–27, 101, 901; 600/407, 600/410, 411, 425, 427; 128/920, 922
See application file for complete search history.

(56) References Cited

U.S. PATENT DOCUMENTS 5,841,829 A * 11/1998 Dolazza et al. .................... 378/4
7,180,975 B2 * 2/2007 Heuscher et al. ................. 378/4
8,031,828 B1 * 10/2011 DeMan et al. ..................... 378/4
8,582,855 B2 * 11/2013 Koehler ......................... 382/131
2012/0308100 A1 * 12/2012 Pack et al. ..................... 382/131

OTHER PUBLICATIONS

Hsieh, J., A practical Cone Beam Artifact Correction Algorithm, Nuclear Science Symposium Conference Record, IEEE, Oct. 2000, vol. 2., pp. 15/71-15/74.
Maass, C., Dennerlein, F., Noo., F., and Kachelriess, M., Comparing short scan CT Reconstruction Algorithms Regarding Cone-Beam Artifact Performance, Nuclear Science Symposium Conference Record, IEEE, Oct. 30-Nov. 6, 2010, pp. 2188-2193.
Zou, Yu, Zamyatin, Alexander A., Chiang, Beshan S., and Silver, Michael D., "Reduction of the Streak Artifacts in Circular Cone Beam CT Using Scaonograms", IEEE Nuclear Science Symposium Conference Record, M18-294, pp. 3531-3536, 2007.
Zou, Yu, Zamyatin, Alexander A., Chiang, Beshan S., and Silver, Michael D., "Reduction of the streak artifacts in circular cone beam CT using scanograms", IEEE Nuclear Science Symposium and Medical Imaging Conference, Oct. 28-Nov. 3, 2007, Honolulu, Hawaii, USA.
Katsevich, Alexander, "Imaging reconstruction for the circle and line trajectory", Institute of Physics Publishing, Physics in Medicine and Biology, 49 (2004) 5059-5072.

* cited by examiner

*Primary Examiner* — Abolfazl Tabatabai
(74) *Attorney, Agent, or Firm* — Yoshida & Associates, LLC (57) ABSTRACT

Cone beam artifacts arise in circular CT reconstruction. The cone beam artifacts are substantially removed by reconstructing a reference image from measured data at circular source trajectory, generating synthetic data by forward projection of the reference image along a pre-determined source trajectory, which supplements the circular source trajectory to a theoretically complete trajectory, reconstructing a correction image from the synthetic data and substantially reducing the cone beam artifacts by generating a corrected image using the reference image and the correction image.

22 Claims, 8 Drawing Sheets

FIG. 7A
FDK IMAGE

FIG. 7B
SART AFTER 500 ITERATIONS

FIG. 7C
PROPOSED METHOD AFTER 10 ITERATIONS

FIG. 8F
IMAGE D

FIG. 8E
IMAGE D WITH ONE TIME LINE CORRECTION

FIG. 8D
CFK (W/ REBINNING)

METHOD AND SYSTEM FOR SUBSTANTIALLY REDUCING ARTIFACTS IN CIRCULAR CONE BEAM COMPUTER TOMOGRAPHY (CT)

FIELD OF THE INVENTION

The current invention is generally related to an image processing and system, and more particularly related to substantially reducing artifacts in circular cone beam Computer Tomography (CT).

BACKGROUND OF THE INVENTION

Cone beam artifacts are a well known problem in circular computed tomography. The X-ray source cone angle in most advanced CT systems such as Toshiba AquilionONE is quite large, and CFK images suffer cone beam artifacts due to missing data in radon domain.

In one prior art approach, the artifact in circular cone beam CT is substantially removed by applying exact reconstruction based upon a theoretically complete trajectory such as a combination of a circular trajectory and a line trajectory. Although an additional line scan achieves a theoretically complete trajectory with a circular trajectory for exact reconstruction, the additional scan is often either unavailable or impractical to collect. Furthermore, since circular and line data are not simultaneously obtained, any change in motion or agent enhancement between the two scans causes data inconsistency between the two data sets and affect image accuracy. Lastly, the additional scan exposes a patient to additional radiation dose.

For the above reasons, it is of particular interest to accurately reconstruct image volume only from circular data. In another prior art approach, a scanogram is used to estimate a line data. Although this approach does not increase patient's radiation dose, cone beam artifacts are still observable even though the estimated line data helped reduce much of the artifacts. At the same time, any change in motion or agent enhancement is also causing some inaccuracy in the resulted images.

For the above described reasons, it is still desired to have a system and a method for substantially reducing artifacts in circular cone beam Computer Tomography (CT).

DETAILED DESCRIPTION OF THE EMBODIMENT(S)

Figure 1:
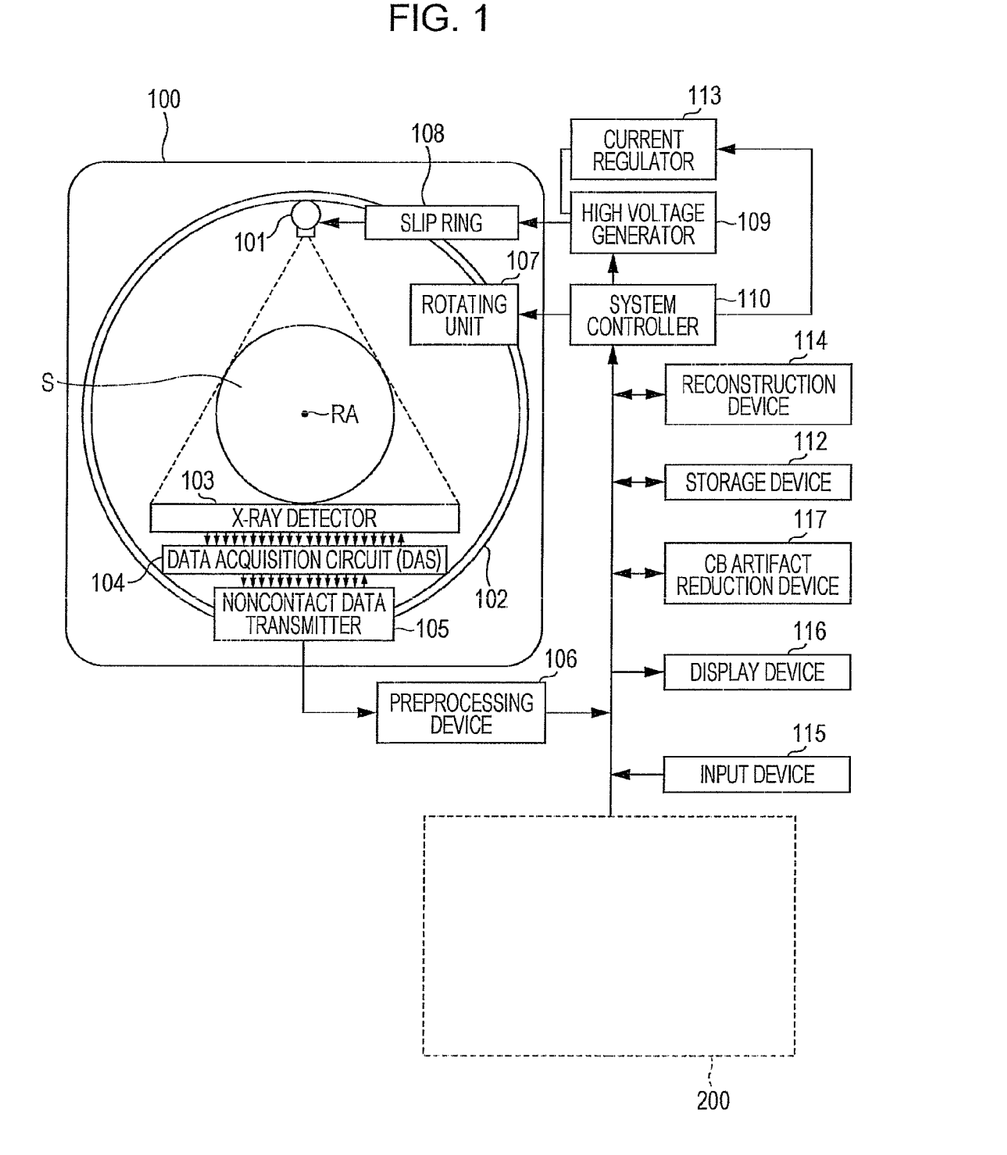
FIG. 1 is a diagram illustrating one embodiment of the multi-slice X-ray CT apparatus or scanner for substantially reducing cone-beam artifacts in images reconstructed from data acquired over circular trajectory according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, multi-scale processing device 117 and the scan plan support apparatus 200. The scan plan support apparatus 200 includes a function for supporting an imaging technician to develop a scan plan.

One embodiment of the reconstruction device 114 further includes various software and hardware components and performs a predetermined analytic reconstruction process on the projection data. According to one aspect of the current invention, the reconstruction device 114 of the CT apparatus advantageously reconstructs an image volume by using a predetermined filtered backprojection (FBP) technique.

According to another aspect of the current invention, the reconstruction device 114 of the CT apparatus advantageously minimizes total variation (TV) using an iterative reconstruction technique. In general, the reconstruction device 114 in one embodiment of the current invention operates the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. The two steps are sequentially implemented in the main loop where a number of iterations were prescribed in one embodiment.

Before the TV minimization step, the projection data undergoes an ordered subsets simultaneous algebraic reconstruction technique (OS-SART). The projection data is grouped into a predetermined number of subsets N each having a certain number of views. During the ordered subsets simultaneous algebraic reconstruction technique (OS-SART), each subset may be sequentially processed in one embodiment. In another embodiment, a plurality of the subsets may be processed in parallel by taking advantage of certain microprocessor such as multiple central processing units (CPU) or a graphics processing unit (GPU). In the total variation (TV) minimization step, one embodiment of the reconstruction device 114 employs a line search strategy to search a positive step size so as to ensure the objective function of the current image volume to be smaller than that of the previous image volume.

During the ordered subsets simultaneous algebraic reconstruction technique (OS-SART), the reconstruction device 114 also performs two major operations. Namely, for each subset N, the reconstruction device 114 re-projects the image volume to form the computed projection data and back-projects the normalized difference between the measured projection and the computed projection data to reconstruct an updated image volume. In further detail, one embodiment of the reconstruction device 114 reprojects the image volume by using the ray tracing technique where no coefficient of the system matrix is cached. Moreover, one embodiment of the reconstruction device 114 simultaneously re-projects all rays in a subset, and this is optionally implemented in parallel. In the back-projection, one embodiment of the reconstruction device 114 uses a pixel-driven technique to back-project all of the nomialized difference projection data in a subset to form the desired updated image volume. Because the reconstruction device 114 back-projects all ray sums, i.e., difference projection data, in a subset to form an image volume, this operation is optionally implemented in parallel too. These operations are applied to every subset N to complete a single OS-SART step. In addition, AWAD is optionally combined.

In addition to the above described components, one embodiment of the current invention further includes various other software modules and hardware components for performing cone beam artifact reduction. According to one aspect of the current invention, a cone beam (CB) artifact reduction device 117 of the CT apparatus advantageously performs cone beam artifact reduction functions for substantially reducing cone beam artifacts under certain situations. In general, the CB artifact has two components including shading and high-contrast cone beams that degrade the image quality. To improve the image quality, shading is corrected by filtering rebinning while high-contrast is corrected by line image in one exemplary process. The above described artifacts will be further described with respect to other diagrams in the current application.

In another embodiment of the current invention, the cone beam (CB) artifact reduction device 117 of the CT apparatus advantageously combines elements of exact reconstruction and iterative reconstruction such as SART to substantially reduce the cone beam artifact. As will be described in more detail, the reconstruction device 114 reconstructs a circular image from the measured projection data that has been acquired using a cone beam source over the circular source trajectory. Subsequently, the CB artifact reduction device 117 forward projects line data from the circular image, and then the reconstruction device 114 reconstructs a line image based upon the forward projected line data. Based upon the above steps, the CB artifact reduction device 117 combines the circular image and the line image. The combined image contains substantially reduced CB artifacts, which otherwise exist in a conventionally reconstructed image. Finally, the CB artifact reduction device 117 outputs the corrected image.

In one embodiment according to the current invention, the cone beam artifact reduction device 117 is operationally connected to other software modules and or system components such as the storage device 112, the reconstruction device 114, the display device 116 and the input device 115 via a data/control bus. In this regard, the cone beam artifact reduction device 117 alone does not necessarily perform the cone beam artifact functions and or their associated tasks in other embodiments according to the current invention. Furthermore, the cone beam artifact reduction device 117 is optionally a part of other devices such as the reconstruction device 114 in alternative embodiments according to the current invention.

Figure 2:
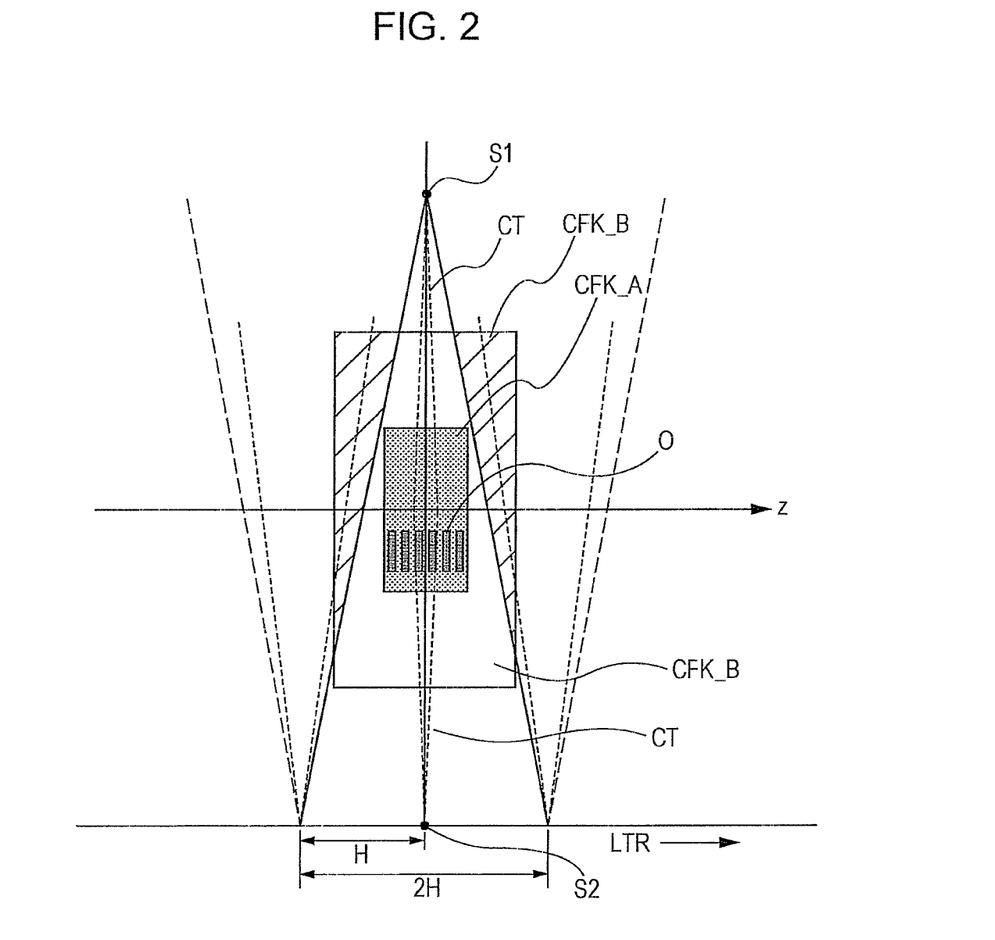
FIG. 2 is a diagram illustrating one aspect of the cause for cone beam (CB) artifacts to be substantially reduced by one embodiment according to the current invention.

FIG. 2 is a diagram illustrating one aspect of the cause for cone beam (CB) artifacts to be substantially reduced by one embodiment according to the current invention. The diagram illustrates an exemplary situation where a set of thin objects O is located at a relative position with respect to a source over a predetermined circular trajectory CT. Cone beam at a source position S1 emits toward the object O with a predetermined cone beam angle. The exemplary situation also illustrates that images are often reconstructed in a zoomed or desired field-of-view (FOV) with better resolution for a diagnostic purpose. Since information on an entire object attenuating the x-ray beam is necessary for forward projection, two volume images CFK_A and CFK_B are generated as illustrated in FIG. 2. The shaded areas correspond to insufficiently acquired measured data. The image CFK_A has the desired FOV to be used in the final result while the image CFK_B has a full FOV for generating missing line data. A required range 2H is shown along a line data direction LTD for generating the line data.

Figure 3:
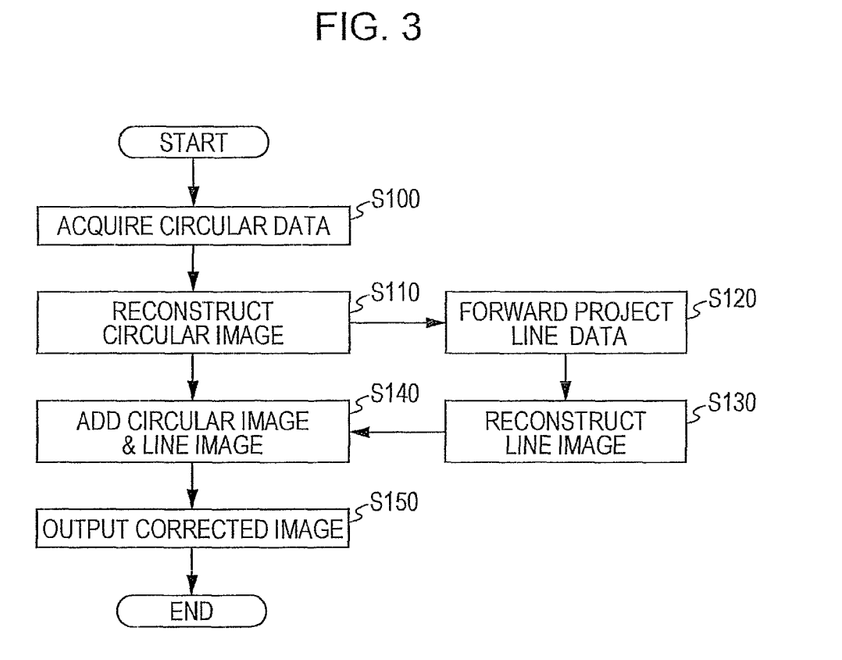
FIG. 3 is a flow chart illustrating general steps involved in an exemplary process of substantially reducing the cone beam (CB) artifacts according to the current invention.

Now referring to FIG. 3, a flow chart illustrates general steps involved in an exemplary process of substantially reducing the cone beam (CB) artifacts according to the current invention. In fact, the flow chart is a conceptual scheme of exemplary process of substantially reducing the cone beam (CB) artifacts according to the current invention, and the current invention is not necessarily limited to the following description. In a step S100, measured data is acquired. In general, the acquired measured data is susceptible to cone beam artifacts if it is reconstructed in a conventional manner since it is insufficient due to a cone beam circular scanning geometry. In a step S110, a circular image is reconstructed from the measured data that has been acquired using a cone beam source over the circular source trajectory. The reconstructed circular image is optionally stored in a predetermined storage to be retrieved later. In a step S120, line data is forward projected or reprojected from the circular image that has been reconstructed in the step S110. The detail of the line data generation in the step S120 will be later described with respect to other flow charts. In a step S130, a line image is reconstructed based upon the forward projected line data that has been generated in the step S120. Based upon the above steps S110, S120 and S130, the circular image and the line image are now combined in a step S140. The combined image contains substantially reduced CB artifacts, which otherwise exist in a conventionally reconstructed image. Finally, the corrected image is outputted in a step S150 for display or analysis. In another embodiment of the substantially reducing CB artifact, some of the above described steps are iteratively repeated using a known iterative technique such as SART to improve accuracy of the line data and in turn the artifact reduction in the outputted image.

Figure 4:
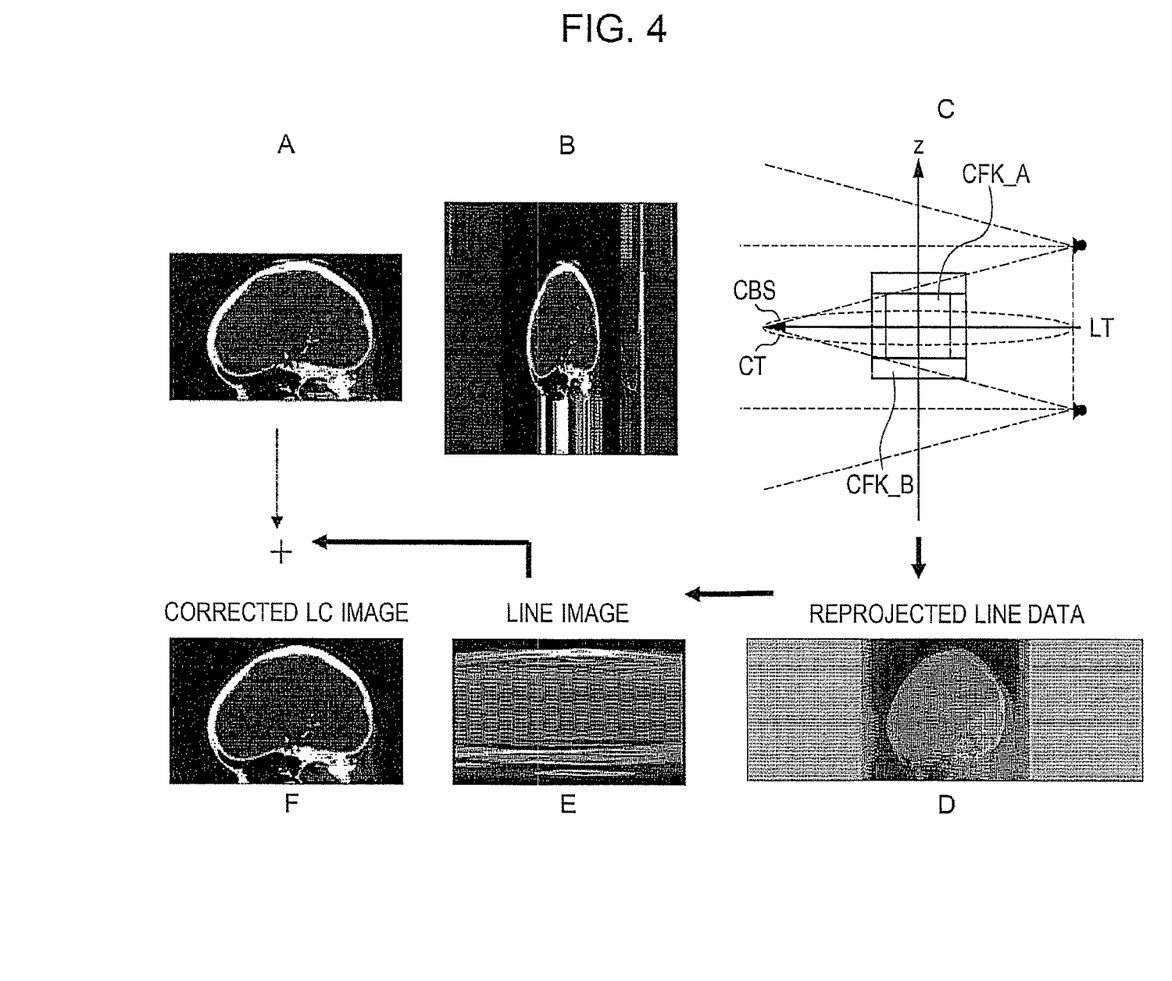
FIG. 4 is a collection of diagrams illustrating a certain conceptual solution for substantially reducing cone beam artifacts by one embodiment according to the current inventions.

FIG. 4 is a collection of diagrams illustrating a certain conceptual solution for substantially reducing cone beam artifacts by one embodiment according to the current inventions. As already described with respect to FIG. 2, an exemplary situation requires a zoomed or desired field-of-view (FOV) with better resolution for a diagnostic purpose. Since information on an entire object attenuating the x-ray beam is necessary for forward projection, two images CFK_A and CFK_B as illustrated in FIGS. 4A and 4B are reconstructed using circular Feld-Kamp (CFK) technique from corresponding circular data that is acquired using a cone beam source CBS over the circular trajectory CT as illustrated in FIG. 4C. FIG. 4C also illustrates that the circular data for the image volume CFK_A is a zoomed portion of the circular data for the image CFK_B. That is, the image CFK_A has a desired FOV within a full or large FOV of the image CFK_B, and the full FOV is extended along the Z axial direction.

According to one embodiment, the line data as illustrated in FIG. 4D is generated from forward projection of the filtered back-projected volume image CFK_B according to the current invention. In this regard, reprojection is synonymously used with forward projection in the above described line data generation in the current application. As described above, the image CFK_B has a full FOV. Since x-rays with a large cone angle may pass through space in the Z direction beyond the reconstructed image, the image CFK_B is optionally extended over some Z-range that depends on the scanned system's cone angle. In other embodiments, to reduce the cone beam artifacts in the image CFK_B, a predetermined adaptive low-pass 3D filter is applied to the image CFK_B before the forward projection along a line trajectory LT. Alternatively, a predetermined factorization approach is applied to the image CFK_B before the forward projection along a line trajectory LT in another embodiment.

After the line data is obtained by reprojection of the image CFK_B from line trajectory, a line image with the desired FOV as illustrated in FIG. 4E is reconstructed from the line data as illustrated in FIG. 4D in one embodiment of the cone beam artifact reduction process according to the current invention. Finally, the line image with the desired FOV as illustrated in FIG. 4E is combined as indicated by a plus sign with the image volume CFK_A as illustrated in FIG. 4A to generate a corrected image as illustrated in FIG. 4F. The combined image has substantially reduced cone beam artifacts. In one embodiment, the image volume CFK_B is optionally updated by adding an image reconstructed from the line data with a full FOV. Furthermore, since the line data is forward projected from a volume image with artifacts, it is approximated data. For this reason, in another embodiment, an iterative approach is used to refine the line data and improve the cone beam artifact reduction.

Figure 5:
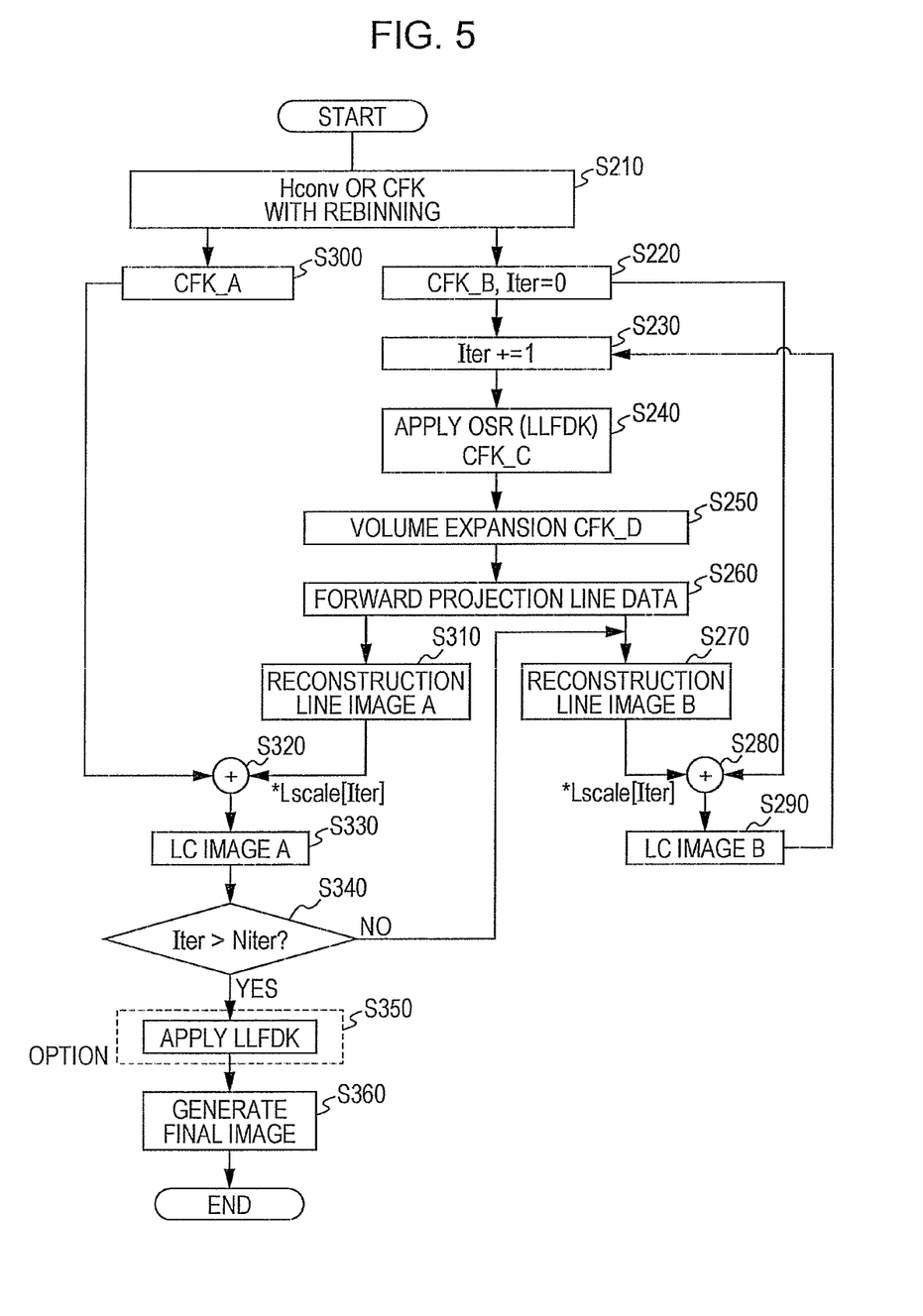
FIG. 5 is a flow chart illustrating steps involved in the cone beam artifact reduction process in one embodiment according to the current invention.

FIG. 5 is a flow chart illustrating steps involved in the cone beam artifact reduction process in one embodiment according to the current invention. In an exemplary process of substantially reducing cone beam artifacts, it is assumed that the measured data has been acquired by a predetermined circular data acquisition technique using a certain conebeam angle. In general, the cone beam artifact reduction process in the embodiment generates two reference images CFK_A and CFK_B respectively having a small desired field of view and a full field of view from the corresponding circular cone beam data. The cone beam artifact reduction process in the embodiment generates synthetic data by forward projecting the reference image CFK_B having the full field of view along a predetermined source trajectory and then reconstructs a correction image from the synthetic data. The correction is achieved because the predetermined source trajectory such as a line trajectory supplements the circular source trajectory of the reference image CFK_B. Furthermore, the cone beam artifact reduction process in the embodiment iteratively repeats certain steps such as steps S230 through S290 with respect to the line image so that a corrected image after a step S360 has substantially reduced cone beam artifacts according to the current invention. In alternative embodiments, the cone beam artifact reduction process performs line image manipulation in a predetermined manner in lieu of iteration.

Still referring to FIG. 5, the process of substantially reducing the cone beam artifact is further described in detail. In general, reference images are obtained based upon a filtered-backprojection algorithm by filtering along predetermined filtering directions that are given by Cseg+z/cos (gamma), where gamma is a cone angle, z is a vertical distance from Cseg, which is defined by a number of detector rows—1 divided by 2. In a step S210, the measured data undergoes a predetermined Hconv step, which outputs the convolved data to reconstruct two reference images. In one embodiment, the Hconv step utilizes hybrid Ramp plus Hilbert kernels. In another embodiment, the circular Feld-Kamp (CFK) technique is used to generate the two reference images. Additionally, a rebinning step is optionally added to the Hconv step to improve some image quality such as in brain shading for head imaging. In an alternative embodiment, a rebinning step and an inverse rebinning of the convolved data are optionally performed respectively prior and subsequent to the Hconv step to improve some image quality. In a step S300, a first reference image CFK_A is reconstructed from the circular cone beam data using the circular Feld-Kamp (CFK) technique, and the first reference volume image CFK_A has a first field of view (FFOV). The FFOV is generally a desired back projection field of view. Similarly, in a step S220, a second reference image CFK_B is reconstructed from the circular cone beam data, and the second reference volume image CFK_B has a second field of view (SFOV), which is larger than the FFOV and optionally covers a gantry of the CT imaging system. Both reference images CFK_A and CFK_B are now optionally stored in the respective steps S300 and S220 for later retrieval. Furthermore, the step S220 also initializes an iteration counter Iter for the subsequent instances of the steps involved in iteration.

Still referring to FIG. 5, iterative steps in the process of substantially reducing the cone beam artifact are further described in detail. In a step S230, the iteration counter Iter is incremented by one to keep track of a predetermined number of iterations. In a step S240, a predetermined filter such as OSR filter is applied to the second reference volume image CFK_B to generate an image CFK_C, which is a LLFDK-corrected CFK image. Subsequently, the image CFK_C is now volume expanded to an expanded slice CFK_D for forward projection in a step S250. In a step S260, the slice CFK_D is forward projected to line data, and the same line data is reconstructed to a line image A and a line image B respectively in a step S310 and a step S270. Subsequently, the line image B is scaled by a line imaging scaling factor in a step S270 for each iteration, which is combined with the second reference image CFK_B in a step S280 to generate a LC image B in a step S290 before starting a next iteration with the LC image B in the step S230, where the iteration counter Iter is incremented.

By the same token, the line image A is also scaled by the line imaging scaling factor in the S310, which is combined with the first reference image CFK_A in a step S320 to generate a LC image A in a step S330. It is determined whether or not a value of the iteration counter Iter is larger than a predetermined number of iterations Niter in a step S340. If it is determined in the step S340 that the Iter counter value is not larger than the max iteration value Niter, the predetermined number of iterations has not yet been completed, and the process of substantially reducing the cone beam artifact proceeds to the step S260 for further iteration. On the other hand, if it is determined in the step S340 that the Iter counter value is larger than the max iteration value Niter, the predetermined number of iterations has been completed, and the process of substantially reducing the cone beam artifact optionally apply the LLFDK-correction in a step S350 before generating a corrected final image in a step S360. The process of substantially reducing the cone beam artifact is not limited to the above descriptions and includes other implementation steps according to the current invention.

Figure 6A:
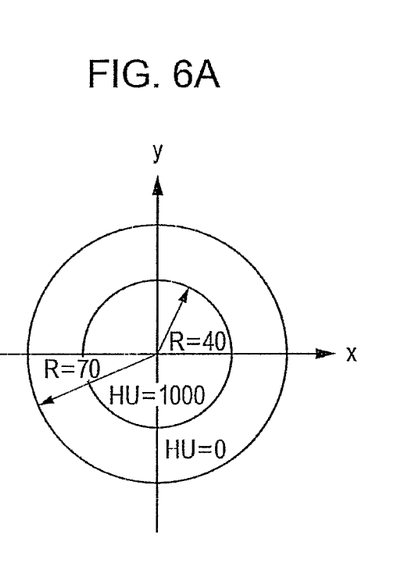
FIGS. 6A and 6B are diagrams respectively illustrating a side view and a top view of a disk phantom that is used to evaluate the effects in the substantial cone beam artifact reduction in example embodiments according to the current invention.
Figure 6B:
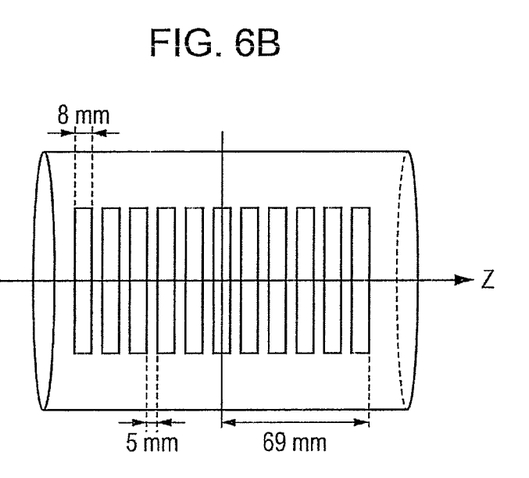

FIGS. 6A and 6B respectively illustrate a side view and a top view of a disk phantom that is used to evaluate the effects in the substantial cone beam artifact reduction in example embodiments according to the current invention. The phantom has the disc-like splits along the Z direction.

Figure 7A:
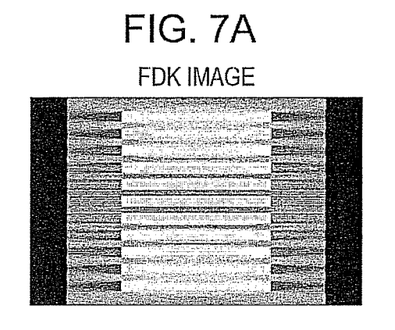
FIG. 7A shows a conventional FDK image reconstructed from the disc phantom without any cone beam artifact correction.
Figure 7B:
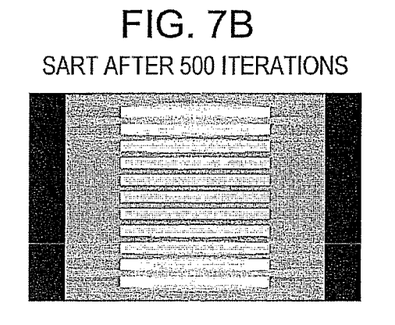
FIG. 7B shows a SART image reconstructed the disc phantom after 500 iterations without any cone beam artifact correction.
Figure 7C:
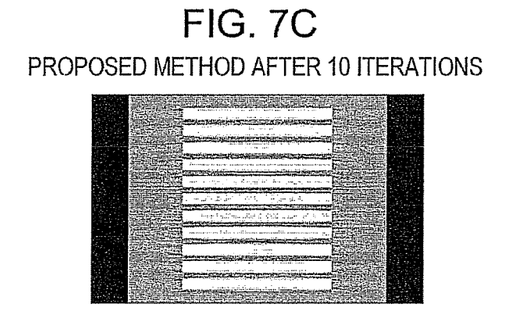
FIG. 7C shows a corrected image reconstructed from the disc phantom with one exemplary process for substantially reducing the cone beam artifact according to the current invention.

FIGS. 7A, 7B and 7C illustrate the effects of the substantial cone beam artifact reduction in one, examplary comparison according to the current invention. FIG. 7A shows a conventional FDK image reconstructed from the disc phantom without any cone beam artifact correction. A significant cone beam artifact is observed. FIG. 7B shows a SART image reconstructed from the disc phantom after 500 iterations without any cone beam artifact correction. FIG. 7C shows a corrected image reconstructed from the disc phantom with one exemplary process for substantially reducing the cone beam artifact according to the current invention. The significant cone beam artifact is substantially reduced.

Figure 8A:
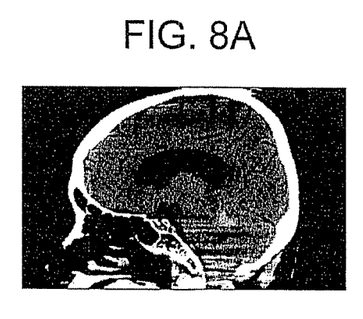
FIG. 8A shows a reconstructed image using CFK without rebinning.
Figure 8B:
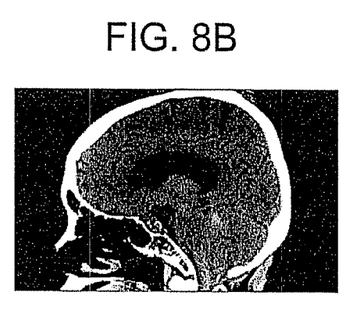
FIG. 8B shows a reconstructed image using CFK without rebinning but with the OSR filtering.
Figure 8C:
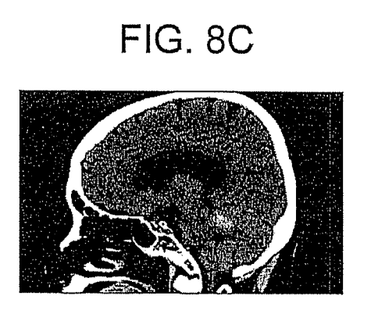
FIG. 8C shows a reconstructed image using HFK for comparison.
Figure 8D:
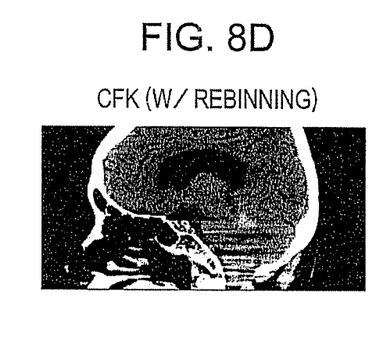
FIG. 8D shows a reconstructed image using CFK with rebinning.
Figure 8E:
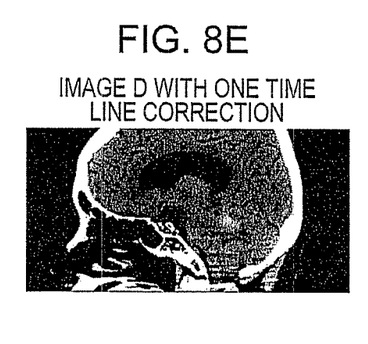
FIG. 8E shows a reconstructed image using CFK with rebinning and one-time forward projected line data correction according to the process of substantially reducing the cone beam artifact of the current invention.
Figure 8F:
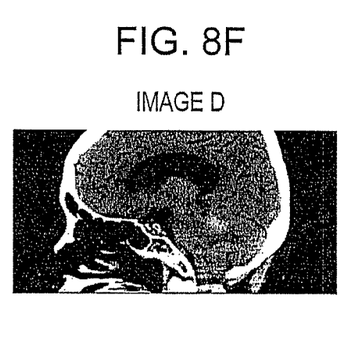
FIG. 8F shows a reconstructed image using CFK with rebinning and three-time iterative forward projected line data correction according to the process of substantially reducing the cone beam artifact of the current invention.

FIGS. 8A through 8F illustrate the effects of the substantial cone beam artifact reduction in another exemplary comparison according to the current invention. The exemplary images in FIGS. 8A through 8F is generated from thick MPR slices of clinical head data using a CFK or HFK reconstruction technique. Furthermore, the exemplary images in FIGS. 8A through 8F are generated using a combination of the line correction, data rebinning and the OSR correction. In addition, FIG. 8A shows a reconstructed image using CFK without rebinning. FIG. 8B shows a reconstructed image using CFK without rebinning but with the OSR filtering. FIG. 8C shows a reconstructed image using HFK for comparison. FIG. 8D shows a reconstructed image using CFK with rebinning. FIG. 8E shows a reconstructed image using CFK with rebinning and one-time forward projected line data correction according to the process of substantially reducing the cone beam artifact of the current invention. FIG. 8F shows a reconstructed image using CFK with rebinning and three-time iterative forward projected line data correction according to the process of substantially reducing the cone beam artifact of the current invention.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of correcting cone beam artifacts in circular computed tomography, comprising the steps of:
    a) reconstructing a reference image from measured data at a predetermined circular source trajectory, the reference image being obtained based upon a filtered-backprojection algorithm by filtering along predetermined filtering directions, the predetermined filtering directions being given by Cseg+z/cos (gamma), where gamma is a cone angle, z is a vertical distance from Cseg, which is defined by a number of detector rows—1 divided by 2;
    b) generating synthetic data by forward projection of the reference image along a predetermined source trajectory, which supplements the circular source trajectory to a theoretically complete trajectory;
    c) reconstructing a correction image from the synthetic data; and
    d) substantially reducing the cone beam artifacts by generating a corrected image using the reference image and the correction image.

2. The method of correcting cone beam artifacts in circular computed tomography according to claim 1 wherein the reference image is one of a circular Feldkamp (CFK) image and a Hybrid convolution reconstruction (Hconv) image.

3. The method of correcting cone beam artifacts in circular computed tomography according to claim 1 wherein the correction image is a line scan reconstruction image.

4. The method of correcting cone beam artifacts in circular computed tomography according to claim 1 further comprising additional step f) of iterating the steps b) through d) using the corrected image as the reference image in the step b) for a predetermined number of times.

5. The method of correcting cone beam artifacts in circular computed tomography according to claim 1 wherein a low pass filter is applied in the step b).

6. The method of correcting cone beam artifacts in circular computed tomography according to claim 1 wherein the step a) generates a first circular image and a second circular image from the measured circular data, the first circular image has a full field of view while the second circular image is a desired field of view.

7. The method of correcting cone beam artifacts in circular computed tomography according to claim 6 wherein the step b) applies a predetermined OSR filter to the first circular image.

8. The method of correcting cone beam artifacts in circular computed tomography according to claim 7 wherein the step b) forward projects the first circular image to generate forward projected line data.

9. The method of correcting cone beam artifacts in circular computed tomography according to claim 8 wherein the step c) reconstructs an line image from the forward projected line data.

10. The method of correcting cone beam artifacts in circular computed tomography according to claim 9 wherein the step d) substantially reduces the cone beam artifacts by generating the corrected image using the second circular image and the line image.

11. The method of correcting cone beam artifacts in circular computed tomography according to claim 10 further comprising additional step f) of iterating the steps b) through d) using the corrected image as the reference image in the step b) for a predetermined number of times.

12. A system for correcting cone beam artifacts in circular computed tomography, comprising:
  a reconstruction device for reconstructing a reference image from measured data at a predetermined circular source trajectory, the reference image being obtained based upon a filtered-backprojection algorithm by filtering along predetermined filtering directions, the predetermined filtering directions being given by Cseg+z/cos (gamma), where gamma is a cone angle, z is a vertical distance from Cseg, which is defined by a number of detector rows—1 divided by 2; and
  a cone beam artifact reduction device connected to said reconstruction device for generating synthetic data by forward projection of the reference image along a predetermined source trajectory, which supplements the circular source trajectory to a theoretically complete trajectory, wherein said reconstruction device reconstructs a correction image from the synthetic data and said cone beam artifact reduction device substantially reduces the cone beam artifacts by generating a corrected image using the reference image and the correction image.

13. The system for correcting cone beam artifacts in circular computed tomography according to claim 12 wherein the reference image is one of a circular Feldkamp (CFK) image and a Hybrid convolution reconstruction (Hconv) image.

14. The system for correcting cone beam artifacts in circular computed tomography according to claim 12 wherein the correction image is a line scan reconstruction image.

15. The system for correcting cone beam artifacts in circular computed tomography according to claim 12 wherein said reconstruction device and said cone beam artifact reduction device iterate for a predetermined number of iterations using the corrected image as the reference image.

16. The system for correcting cone beam artifacts in circular computed tomography according to claim 12 wherein said reconstruction device utilizes a low pass filter.

17. The system for correcting cone beam artifacts in circular computed tomography according to claim 12 wherein said reconstruction device generates a first circular image and a second circular image from the measured circular data, the first circular image has a full field of view while the second circular image is a desired field of view.

18. The system for correcting cone beam artifacts in circular computed tomography according to claim 17 wherein said cone beam artifact reduction device applies a predetermined OSR filter to the first circular image.

19. The system for correcting cone beam artifacts in circular computed tomography according to claim 18 wherein said cone beam artifact reduction device forward projects the first circular image to generate forward projected line data.

20. The system for correcting cone beam artifacts in circular computed tomography according to claim 19 wherein said reconstruction device reconstructs an line image from the forward projected line data.

21. The system for correcting cone beam artifacts in circular computed tomography according to claim 20 wherein said cone beam artifact reduction device substantially reduces the cone beam artifacts by generating the corrected image using the second circular image and the line image.

22. The system for correcting cone beam artifacts in circular computed tomography according to claim 21 wherein said reconstruction device and said cone beam artifact reduction device iterate for a predetermined number of iterations using the corrected image as the reference image.

* * * * *